(12) United States Patent
Lin

(10) Patent No.: US 8,911,500 B2
(45) Date of Patent: *Dec. 16, 2014

(54) METHOD OF A PHARMACEUTICAL DELIVERY SYSTEM FOR USE WITHIN A JOINT

(71) Applicant: Abraham Lin, Huntington Beach, CA (US)

(72) Inventor: Abraham Lin, Huntington Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/831,790

(22) Filed: Mar. 15, 2013

(65) Prior Publication Data

US 2014/0277515 A1 Sep. 18, 2014

(51) Int. Cl.
*A61F 2/30* (2006.01)
*A61F 2/28* (2006.01)
*A61L 27/54* (2006.01)

(52) U.S. Cl.
CPC ...................................... *A61L 27/54* (2013.01)
USPC ................... 623/18.11; 623/16.11; 623/23.57

(58) Field of Classification Search
CPC .................................... A61F 2/38; A61F 2/281
USPC .......... 623/16.11, 11.11, 18.11, 22.11, 19.11, 623/20.14, 23.57–23.59
See application file for complete search history.

(56) References Cited

U.S. PATENT DOCUMENTS

| | | | |
|---|---|---|---|
| 2004/0186576 A1* | 9/2004 | Biscup et al. | 623/17.12 |
| 2006/0222681 A1* | 10/2006 | Richard | 424/426 |
| 2008/0086199 A1* | 4/2008 | Dave et al. | 623/1.42 |
| 2012/0101578 A1* | 4/2012 | Lee | 623/17.16 |

* cited by examiner

*Primary Examiner* — Jason-Dennis Stewart
(74) *Attorney, Agent, or Firm* — Alexander Chen, Esq.

(57) ABSTRACT

Methods and apparatus of providing a joint replacement parts with a pharmaceutical delivery system is provided. The pharmaceutical delivery system is placed within the joint replacement parts to provide, over a period of time, sustained release of a controlled concentration of pharmaceuticals within the joint space of the joint replacement and to produce a local or systemic physiological of pharmacological effect.

5 Claims, 16 Drawing Sheets

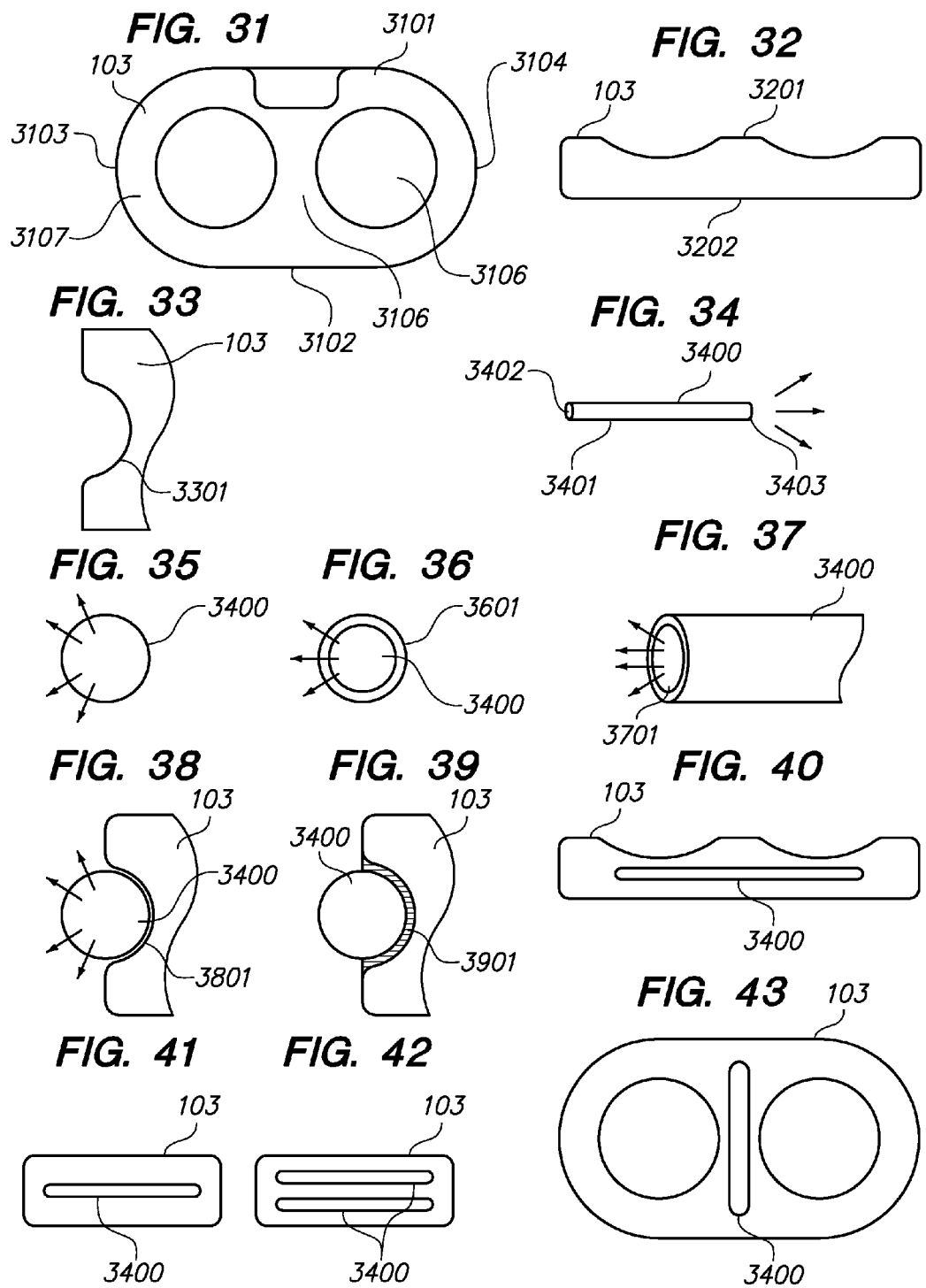

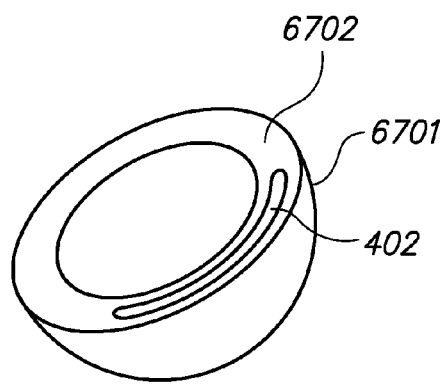
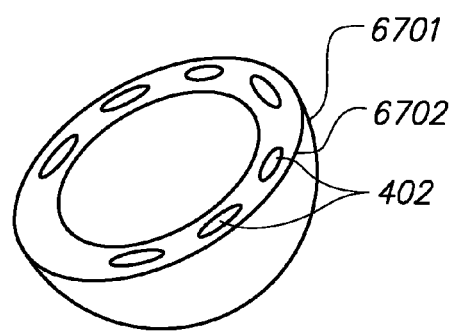
FIG. 67   FIG. 68

METHOD OF A PHARMACEUTICAL DELIVERY SYSTEM FOR USE WITHIN A JOINT

INCORPORATION BY REFERENCE

This is a continuation in part application claiming priority to application Ser. No. 13/409,114 which was filed on Mar. 1, 2012 with the title "Method of a Pharmaceutical Delivery System for Use Within a Joint Replacement" which claims the benefit of priority under 35 U.S.C. 119(e) to the filing date of U.S. provisional patent application No. 61/560,032 "Pharmaceutical Drug Delivery System" which was filed on Nov. 15, 2011, and which is incorporated herein by reference in its entirety.

FIELD OF THE INVENTION

The present invention pertains to both a novel and useful device for releasing a useful agent. More particularly, the invention relates to a pharmaceutical delivery device having means for changing its release rate pattern for the subsequent release of the agent at a controlled and continuous rate over a prolonged period of time to obtain a desired local or systemic physiological or pharmacological effect. Specifically, the invention concerns a pharmaceutical delivery system for introduction into a joint replacement for the purpose of delivering a local concentration of an agent, such as pharmaceuticals, within the effective joint space, wherein the joint replacement may be, for example, a knee, hip or shoulder joint replacement. The methods allow sustained release of a pharmaceutical or multiple pharmaceuticals into a joint space in which the replacement parts reside, wherein the pharmaceutical agent may be used to treat infection, pain, inflammation, or osteolysis, or to prevent weakening of the bone-cement interface or bone-prosthesis interface.

BACKGROUND OF THE INVENTION

A Synovial joint, also known as a diathrosis, is a common and movable type of joint in the body. Synovial joints achieve movement at the point of contact of the articulating bones. A synovial joint is a part of the body where two adjacent bones are coupled and encapsulated within a synovial membrane, wherein the presence of synovial fluid within those capsules provides lubrication. More specifically, the joints have cartilage which coats the ends of the bones to allow for motion between the two bones without significant friction. Arthritis of a joint, which may arise from a variety of causes, is a debilitating condition that involves wear of the cartilage in a joint resulting in pain, stiffness, and loss of function. Treatment options for arthritis vary depending on the type of arthritis and include orthopedic bracing, medications, and joint replacement surgery, among other treatment options.

Joint replacement surgery is an orthopedic procedure that is performed on patients with various forms of arthritis to relieve pain, increase functionality, and improve quality of life. The joint replacement procedure may be performed, for example, on a knee, hip, or shoulder. However, there is about a 1-2% risk of infection in these joint replacements according to relevant literature. In fact, infections can be quite devastating for the patient and would require a surgical washout, followed by long-term intravenous antibiotics over a period of at least six (6) weeks. Chronic infections or infections by treatment-resistant bacteria entail a much more complex and invasive procedure. The surgeon must surgically remove all joint replacement parts. Then, an antibiotic loaded spacer, which makes the joint replacement less functional, is required. Finally, the patient must be treated with intravenous antibiotics for at least six (6) weeks. Once the infection is eradicated, the patient would need another surgical procedure requiring the use of a generally more complex joint replacement part.

Over the years, various pharmaceutical drugs have been developed to assist in the treatment of a wide variety of ailments and diseases. In many instances, however, these pharmaceutical drugs are not capable of being administered either orally or intravenously without substantial risk and detrimental side effects. Therefore, due to these risks and side effects that certain drugs impose, researchers have developed systems for administering these drugs to facilitate treatment of these ailments and diseases. Many of these systems provide for the pharmaceutical delivery device to release the pharmaceutical drugs at a certain rate in order to reduce the occurrence of detrimental side effects. Furthermore, in many therapeutic programs, in order to achieve the desired physiological or pharmacological effect, the pharmaceutical drugs must be administered by the pharmaceutical delivery system and released into the body at a controlled rate and over a prolonged period of time. In fact, in many instances, the rate of release of the drug from the pharmaceutical delivery device should have a zero order time dependence, that is, the rate of drug release is independent of time.

One embodiment of such a pharmaceutical delivery device is an orally administered pill or capsule which contains a drug encapsulated within various layers of a composition that dissolves over a period of time in the digestive tract, thereby allowing gradual or slow release of the drug into the system.

Another embodiment of such a delivery device is to mix a drug with a carrier material that is gradually broken down by body fluids. Therefore, as the carrier disintegrates, the pharmaceutical agent is released. Numerous materials, including waxes, oils, fats, soluble polymers, etc., have been used to serve as the carrier in such a pharmaceutical delivery device. While some of these delivery devices provide a delayed and prolonged release of the pharmaceutical drug, the desired constant rate of release over the extended period of time has not been obtained. One reason for variable rate of release is that as the carrier disintegrates, the surface area of the dosage unit decreases, concomitantly exposing increasingly smaller quantities of the carrier to the surrounding body fluids. This inherently results in a decline in the release rate of the pharmaceutical agent in the body over time.

Another type of device for controlling the administration of the pharmaceutical drugs is by coating the drug with a polymeric material permeable to the passage of the drug to obtain the desired effect. Such devices are particularly suitable for treating a patient when localization of the effect of the pharmaceutical agent is highly desirable, because the pharmaceutical agents can locally target only the designated area without having to expose the patient's entire body to the drug. Localizing the physiological and pharmacological effect of the pharmaceutical drug is advantageous, because any possible side effects of the drug could be minimized. These devices too, however, have inherent drawbacks. For example, a single material, such as silicone rubber polymers (especially polydimethylsiloxane), is generally selected to serve as the diffusion control membrane for the delivery device. These polymers were selected, in large part, because of their permeability to some important drug molecules. The mere high permeability without consideration for the release rate controlling properties, however, can be a significant disadvantage as to defeat the primary object of an acceptable drug delivery device. For example, with many important drug molecules, the diffusion rate through a polydimethylsiloxane membrane is very great, and, in fact, it is often greater than the rate of clearance of the diffused drug from the outer surface of the capsule. As a result, in many instances, the rate limiting step is the clearance of the pharmaceutical drug from the exterior of the capsule, rather than diffusion of the pharmaceutical drug through the capsule wall. As such, the pharmaceutical agent will not be released at the desired rate. Furthermore, clearance rate within the body is difficult to control, because the body is subject to frequent change. This inherently defeats the object of providing a drug delivery device which releases drug at a constant rate over a prolonged period of time.

Another type of device known to the art is to incorporate the pharmaceutical drug into certain type of liquid carriers, usually in microcapsule formulations. These microcapsules, however, are not designed for the controlled release of drugs for a prolonged period of time by using materials suitable for controlling the rate of release of the drugs. The microcapsules are frequently crushable, and they merely function as drug carriers supplying their drug in bulk. Therefore, rupture of the microcapsules results a bulk release rather than in a controlled release the pharmaceutical agents over time. As such, these types of capsules are not suitable for releasing drug at a controlled rate for a prolonged period of time.

The above described systems and devices are intended to provide sustained release rate of pharmaceutical drugs to bring about the desired local or systemic physiological or pharmacological effects. There are, however, many disadvantages associated with their use, including those discussed above. Furthermore, the drug may not be able to reach certain areas of the body via oral or intravenous administration of the drug. It will be appreciated by those versed in the art to which the present invention pertains that the present invention can be locally administered to target specified area as required.

OBJECTIVE OF THE INVENTION

Accordingly, it is an object of the invention to provide a pharmaceutical delivery system, wherein the pharmaceutical delivery system is introduced into a joint replacement.

It is an object of the invention to allow the pharmaceutical delivery system to release a desired concentration of pharmaceutical over a sustained period of time into the joint space in which the joint replacement resides.

It is an object of the invention for the pharmaceutical released from the delivery system to produce a physiological or pharmacological effect.

It is an object of the invention for the pharmaceutical release from the delivery system to locally target only a specific area.

It is an object of the invention to place the pharmaceutical delivery system into the joint replacement part before the index operation.

It is an object of the invention to place the pharmaceutical delivery system into the joint replacement part during the index operation.

It is an object of the invention to place the pharmaceutical delivery system into the joint replacement part before the revision operation.

It is an object of the invention to place the pharmaceutical delivery system into the joint replacement part during the revision operation.

It is an object of the invention to place the pharmaceutical delivery system into the joint replacement during an irrigation and debridement operation.

It is an object of the invention to create a space on a joint replacement part in which to introduce the pharmaceutical delivery system.

It is an object of the invention to use a space that already exists to introduce the pharmaceutical delivery system.

It is an object of the invention for the pharmaceutical to homogenously mix or heterogeneously distribute into a polymeric matrix material.

It is an object of the invention for the pharmaceutical to be coated onto a metal piece that can take the same shape or any shape.

It is an object of the invention for the pharmaceutical delivery system to be attached to the polyethylene or other joint replacement part by an adhesive such as cement or glue.

It is an object of the invention for the pharmaceutical delivery system to be in any shape such as a cylinder, mound, hemisphere, or cube, etc.

It is an object of the invention to use sealant to secure the pharmaceutical delivery system into the recesses of a manufactured replacement part.

It is an object of the invention to use adhesive to secure the pharmaceutical delivery system into the recesses of a manufactured replacement part.

It is an object of the invention to use press fit to secure the pharmaceutical delivery system into the recesses of a manufactured replacement part.

It is an object of the invention to use the retardant itself to secure the pharmaceutical delivery system into the recesses of a manufactured replacement part.

It is an object of the invention to release pharmaceutical via diffusion, wherein the pharmaceutical moves from areas of higher concentration into areas of lower concentration.

It is an object of the invention that the introduction of the pharmaceutical delivery system will not interfere with the function of the joint itself.

It is an object of the invention that the introduction of the pharmaceutical delivery system will not interfere with the mechanical properties relating to the wear of the joint replacement.

SUMMARY OF THE INVENTION

In one embodiment of the invention, disclosed is a method and system to introduce a pharmaceutical delivery device into a joint replacement to effect a physiological or pharmacological response. An exemplary embodiment is a pharmaceutical delivery system in which the pharmaceutical, such as an antibiotic, is kept in the recesses formed in the joint replacement parts and enclosed with retarder.

In a joint replacement, such as that of the hip or knee, a sustained release of high concentration of pharmaceutical drugs may be desirable. In the methods and designs of the invention disclosed herein, existing manufactured joint replacement parts can be used as the site for introducing the pharmaceutical delivery device. More specifically, the inserts, which are parts of the joint replacement parts and are often made of polyethylene, are ideal for the introduction of the pharmaceutical delivery device for various reasons to be discussed herein. In the insert, an area in the non-weight bearing surface is drilled to serve as the site for the placement of the pharmaceutical drug, such as antibiotic or other pharmaceutical drugs. These pharmaceutical drugs may be in pill, tablet, capsule, micro-encapsulated, liquid, or any other form. The space is created on a non-articulating surface of a joint replacement and is small enough such that it does not interfere with the functions of the joint replacement. Furthermore, the pharmaceutical delivery device would not interfere with the mechanical properties or wear characteristics of the polyethylene itself. A material that allows the pharmaceutical drug to diffuse across the member is used to seal the pharmaceutical drug into the polyethylene insert. The type of membrane, or more specifically the material of the membrane, determines the diffusion rate of the pharmaceutical agent across the membrane. As a result, the pharmaceutical drug will diffuse across the membrane to achieve the desired rate of delivery at the desired concentration for a sustained period of time.

The pharmaceutical drug delivery system may be implemented for use to release one or more pharmaceutical agent at a sustained and controlled rate. Particularly, it may use pharmaceuticals that are traditionally administered intravenously or taken orally in a pill form or liquid form In one embodiment of the invention, the pharmaceutical delivery system comprises a pharmaceutical that is mixed with a polymer. The pharmaceutical and polymer mixture is then physically placed in a space artificially created within the polyethylene, and held into place with a sealant, press fit, adhesive, or screw-type mechanism, glue, or any anchoring mechanism. In one embodiment of the invention, the pharmaceutical may be in a paste or liquid form, placed in the space within the polyethylene, and sealed with a retardant that is comprised of any type of polymer.

In one embodiment of the invention, the pharmaceutical delivery system is comprised of polyethylene that has been previously treated with a pharmaceutical on its surface. This pharmaceutical-treated polyethylene delivery system is then introduced into a space within the existing polyethylene.

In one embodiment of the invention, the pharmaceutical delivery system can be introduced either manually or by a machine. In one embodiment, the pharmaceutical system can be introduced before surgery with the use of a machine, drill, or a punch, followed by a sterilization process that does not affect the pharmaceutical properties of the pharmaceutical agent. In one embodiment, the pharmaceutical delivery system can be introduced before the surgery in a sterile environment by a surgeon or a surgeon's assistant. In another embodiment, the pharmaceutical system can also be introduced during the surgery.

In one embodiment, the pharmaceutical delivery system comprises of a pharmaceutical that is homogenously mixed or heterogeneously distributed into a polymeric matrix material. The pharmaceutical agent may elude through the polymeric matrix or the polymeric matrix material that may or may not degrade or dissolve in vivo. As a result, the pharmaceutical drug is released at a controlled pace over a prolonged period of time to obtain the desired physiological or pharmacological effect.

In one embodiment, the pharmaceutical drug delivery device can be a metal piece that is coated with the pharmaceutical agent. More specifically, instead of the pharmaceutical heterogeneously or homogeneously mixed with a type of polymer, the pharmaceutical is coated onto a metal piece that can be in the same shape or in any shape. Furthermore, the metal piece can be attached and placed into the polyethylene in the same way—anchored, glued, or press-fit.

In another embodiment, the pharmaceutical delivery device can be in any shape, such as cylinder, mound, hemisphere, or cube, etc. Furthermore, the pharmaceutical delivery device is attached to the non-weight bearing part of the polyethylene or other joint replacement part by an adhesive such as cement or glue.

Accordingly, what is disclosed is a drug delivery system for the sustained administration of a pharmaceutical into a joint replacement at a controlled rate to produce a beneficial response, the device comprising a body comprising at least one portion of pharmaceutical mixed with at least one portion of polymer; a joint replacement having an insert wherein the insert is drilled to cause an opening to accommodate the body; wherein the body is placed inside the opening without interfering with the joint replacement's normal operation; a membrane sealing the body within the opening; wherein the membrane is comprised of a material which allows for the pharmaceutical to diffuse across the membrane; wherein the material further determines the diffusion rate of the pharmaceutical crossing the membrane.

In one embodiment, the beneficial response is a pharmacological response. In one embodiment, the beneficial response is physiological response. In one embodiment, the joint replacement is a hip replacement. In one embodiment, the joint replacement is a knee replacement. In one embodiment, the pharmaceutical is an antibiotic. In one embodiment, the opening is located at a non weight bearing area of the insert. In one embodiment, the pharmaceutical is in a paste form. In one embodiment, the pharmaceutical is in a liquid form. In one embodiment, the insert is made of polyethylene. In one embodiment, the body is further held within the opening with an adhesive. In one embodiment, the body is further held within the opening with a screw type mechanism. In one embodiment, the body is further held within the opening with a press fit. In one embodiment, the body is further held within the opening with an anchoring mechanism.

In another embodiment, the body is further held within the opening with a sealant. In another embodiment, the drilled is accomplished by a machine process. In another embodiment, the drilled is accomplished by a manual process. In another embodiment, the joint replacement is sterilized after the insert is drilled. In another embodiment, the pharmaceutical is homogeneously mixed with the polymer. In another embodiment, the pharmaceutical is heterogeneously mixed with the polymer.

In yet another embodiment, the body is in a shape of a cylinder. In yet another embodiment, the body is in a shape of a mound. In yet another embodiment, the body is in the shape of hemisphere. In yet another embodiment, the body is in a shape of a cube. In yet another embodiment, the material is a degradable polymer. In yet another embodiment, the polymer is a polytetraflouroethylene. In yet another embodiment, the polymer is a polyester. In one embodiment, the polymer is a silicone. In one embodiment, the material is a combination of one or more polymers. In one embodiment, the polymer is a natural occurring polymer. In one embodiment, the polymer is a synthetic polymer. In one embodiment, the pharmaceutical is mixed with radio-opaque compound.

In another aspect of the invention, a drug delivery system is disclosed for the sustained administration of a pharmaceutical into a joint replacement at a controlled rate to produce a beneficial response, the device comprising a joint replacement having an insert wherein the insert is coated with a pharmaceutical. In one embodiment, the pharmaceutical is an antibiotic.

In yet another aspect of the invention, a method is disclosed to delivery drug for the sustained administration of a pharmaceutical into a joint replacement at a controlled rate to produce a beneficial response, the method comprising: providing a body comprising at least one portion of pharmaceutical mixed with at least one portion of polymer; preparing a joint replacement having an insert wherein the insert contains an opening; placing the body inside the opening without interfering with the joint replacement's normal operation; sealing the body within the opening with a membrane; wherein the membrane is comprised of a material which allows for the pharmaceutical to diffuse across the membrane; wherein the material further determines the diffusion rate of the pharmaceutical crossing the membrane.

In one embodiment, the joint replacement is sterilized after the insert is drilled. In one embodiment, the pharmaceutical is heterogeneously mixed with the polymer. In one embodiment, the body is in a shape of a cylinder. In one embodiment, the body is in a shape of a mound. In one embodiment, the body is in shape of hemisphere. In one embodiment, the body is in a shape of a cube.

In one embodiment, the material is a degradable polymer. In one embodiment, the polymer is a polytetraflouroethylene. In one embodiment, the polymer is a polyester. In one embodiment, the polymer is a silicone. In one embodiment, the material is a combination of one or more polymers. In one embodiment, the polymer is a naturally occurring polymer. In one embodiment, the polymer is a synthetic polymer. In one embodiment, the pharmaceutical is mixed with radio-opaque compound.

BRIEF DESCRIPTION OF THE DRAWINGS

These and other features and advantages of the invention will not be described with reference to the drawings of certain preferred embodiments, which are intended to illustrate and not to limit the invention, and in which:

FIG. 31 illustrates the top view of the polyethylene insert, its posterior, anterior, medial, and lateral, weight bearing surface, non weight bearing surfaces.

FIG. 32 illustrates the front view of the polyethylene part, with the top surface and undersurface where a recess or recesses can be created.

FIG. 33 illustrates a close up of a usable surface of the polyethylene part, with an exemplary recess.

FIG. 34 illustrates a polymer rod with pharmaceutical, and the exemplary surfaces where pharmaceutical can be released.

FIG. 35 illustrates the cross section of a polymer rod, and one exemplary way of releasing pharmaceutical through the body of the rod.

FIG. 36 illustrates the cross section of a polymer rod which, in this embodiment, is encased with a retardant that controls the release rate of the pharmaceutical from the rod.

FIG. 37 illustrates the side view of a rod which, in this embodiment, has a retardant cap at one end that controls the release rate of the pharmaceutical.

FIG. 38 illustrates a rod within a groove on the polyethylene part and held within by friction fit. The rod's exposure, in this embodiment, controls the release rate of the pharmaceutical.

FIG. 39 illustrates, in this embodiment, a rod held within the recess by an adhesive.

FIG. 40 illustrates the front view of the polyethylene and the appearance of the rod on this surface.

FIG. 41 illustrates the side view of the polyethylene with rod in place.

FIG. 42 illustrates multiple rods within a polyethylene part.

FIG. 43 illustrates the top surface of a polyethylene part with a single rod in place.

FIG. 67 illustrates the face of a polyethylene part of a hip replacement with a pharmaceutical delivery device mounted on its lip.

FIG. 68 illustrates the face of a polyethylene part of a hip replacement with multiple shorter pharmaceutical delivery devices mounted on its lip at various locations.

DETAIL DESCRIPTION OF THE INVENTION

Figure 1:
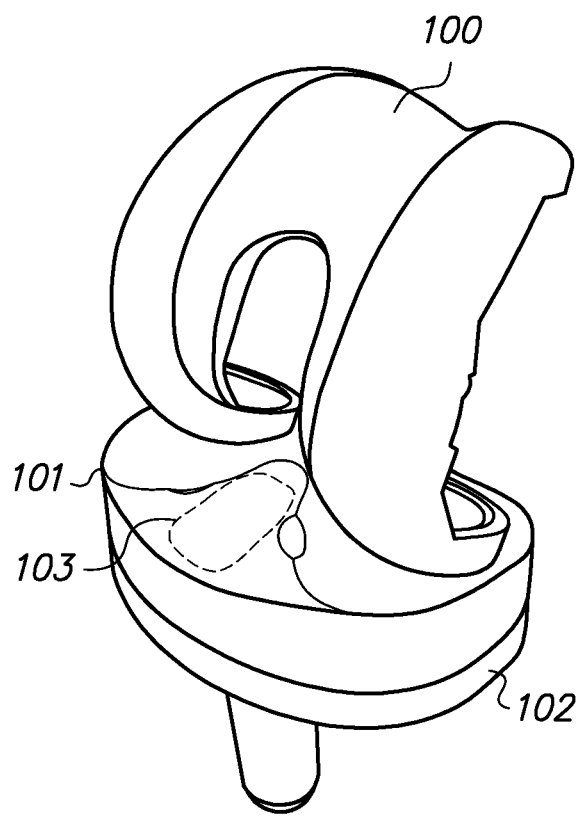
FIG. 1 is an illustrative overview of a total knee joint replacement system and the pharmaceutical delivery device.

In accordance with the practice of the present invention, the pharmaceutical delivery device provides many important advantages over those of the prior art. One advantage is the ease of construction and implementation of the pharmaceutical delivery device into the joint replacement parts using standard manufacturing techniques. The present invention is adaptable to the various sizes, shapes, and forms of the different joint replacement parts; therefore, there is no need to manufacture specialized joint replacement parts for the device to function. As such, the pharmaceutical delivery device disclosed herein can complement any joint replacement part to deliver pharmaceutical agents locally or systematically to effect the desired physiological or pharmacological response.

The method and designs of the pharmaceutical drug delivery device for joint replacements in the present invention may be used at the index procedure in higher risk patients to deliver antibiotic at a sustained dosage to prevent acute infections from occurring in the first place. The system may also be used to deliver an antibiotic for a sustained period of time in the setting of infection at a second operation that requires a surgical washout of the joint replacement. Moreover, the system may be used to deliver antibiotics in the setting of a revision joint replacement that is performed as a result of infection or any other causes. In addition, the system may also be used to deliver, instead of antibiotics, a drug that can disrupt the glycocalyx protecting the bacteria from antibiotics.

Joint replacement surgeries are generally painful and recoveries are generally long—sometimes requiring three (3) months off work, travel, and/or participation in physical fitness activities. Under these circumstances, the pharmaceutical delivery system may be used to deliver anti-inflammatory medication or analgesic medication at the index or revision joint replacement surgery to allow for pain control and quicker rehabilitation.

A significant percentage of joint replacement surgeries are complicated by excessive scarring and stiffness. This often leads to additional operations, and the results are frequently poor. The pharmaceutical delivery system may be used to deliver an anti-scar forming medication.

Moreover, there is often significant bleeding into the joint space of the joint replacement surgery that can result in stiffness, pain, drainage, and repeat operations. The pharmaceutical delivery system may be used to delivery an anti-bleeding medication.

Typically, joint replacement surgeries are prone to failure over time from a process called osteolysis, which is the disruption of the bond between the bone and cement or between the prosthesis and bone. Additionally, as the age of the patient decreases, the burden of the revision surgery increases exponentially. In these circumstances, the pharmaceutical delivery system may be used to deliver a bone supportive medication at the index or revision joint replacement to prevent the disruption of the bone-cement interface or bone-implant interface.

The present invention provides a method for a pharmaceutical delivery system to be placed in a joint replacement, wherein a desired concentration of pharmaceutical can be released, in a sustainable manner, over a period of time.

To implement the pharmaceutical delivery device, an area in the non-weight bearing surface is drilled for the placement of the pharmaceutical drug, such as antibiotic or other drugs. The pharmaceutical drug may be in either a pill, tablet, capsule, micro-encapsulated, liquid, or any form. A material that allows diffusion of the pharmaceutical agent across the membrane, wherein the type of membrane determines the diffusion rate of the pharmaceutical agent, is used to seal the pharmaceutical agent into the polyethylene insert. As a result, the pharmaceutical agent will diffuse across the membrane to achieve the desired delivery at the desired concentration for a period of time.

In one embodiment, the pharmaceutical delivery system comprises of a pharmaceutical agent that is homogenously mixed or heterogeneously distributed into a polymeric matrix material, wherein the material may be a degradable polymer, a polytetraflouroethylene, a polyester, a silicone, or a combination of any polymers. The material may also be a non-degradable polymer. Additionally, the material may be formed of a synthetic or naturally occurring polymer. The pharmaceutical agent may elude through the polymeric matrix, or the polymeric matrix material may degrade or dissolve in vivo, resulting in a controlled release of the pharmaceutical agent to locally or systemically effect a physiological or pharmacological response over a period of time.

The pharmaceutical formulation may be in any form, and the pharmaceutical mixed with the polymer may be in any form. The formulation may be in a viscous form, elastic form, or more rigid, or it may be paste-like, rubber-like, or more firm, and it may have similar properties as that of the polyethylene into which the formulation is being placed.

In one embodiment, the pharmaceutical drug delivery device can be a metal piece that is coated with the pharmaceutical agent. Specifically, instead of a pharmaceutical heterogeneously or homogeneously mixed with a type of polymer, the pharmaceutical is coated onto a metal piece. Like the pharmaceutical mixed with polymer, the metal piece can also take on several shapes as that of the plastic to accommodate the polyethylene insert. The metal piece coated with pharmaceuticals would be functionally equivalent to that of the pharmaceutical and polymeric matrix material mixture. Furthermore, similarly to the pharmaceutical and polymer mixture, the metal piece can be attached and placed into the polyethylene in the same way-anchored, glued, or press-fit.

The pharmaceutical delivery system can be introduced into the joint space manually and held into place with a press fit, screw-type mechanism, glue, or any anchoring mechanism. The pharmaceutical delivery system can also be sealed into place or be additionally treated with a layer of sealant that controls the diffusion of pharmaceutical into the joint space to bring about the desired physiological or pharmacological effect.

In another embodiment, the delivery system is comprised of polyethylene that has been treated with a pharmaceutical. The surface may be treated, for example, with abrasion and coated with a pharmaceutical. This surface would be contiguous with the joint space such that it allows delivery of the pharmaceutical into the joint space. The pharmaceutical delivery system is then introduced into the existing polyethylene once space is created using methods described above.

In one embodiment, the pharmaceutical delivery system is introduced into a space in a joint replacement part that already exist. This pre-existing space functions as a naturally occurring reservoir within the joint replacement parts within which the pharmaceutical delivery system may reside. The pharmaceutical delivery system would be introduced into these reservoirs using the techniques introduced above.

In one embodiment, the pharmaceutical delivery system can be implemented without drilling any of the joint replacement parts. More specifically, the pharmaceutical delivery system can be in any shape, such as a cylinder, mound hemisphere, or cube shaped. This pharmaceutical delivery system is then attached to the polyethylene or other joint replacement part by an adhesive such as cement or glue. The pharmaceutical delivery system would attach to the non-weight bearing surfaces of the joint replacement parts. Furthermore, the pharmaceutical agent may be mixed with a radio-opaque compound allowing the pharmaceutical to be visible on radiographs. As such, physicians would be able to track it and confirm that the adhesive bond has not been broken on subsequent films.

The pharmaceutical delivery system may include any drug in any form; more specifically, it may include, but is not limited to those traditionally used intravenously, in liquid, gel, pill, tablet, capsule, micro-encapsulated, suspension, or other such form. Furthermore, the pharmaceutical itself may be any drug or biological agent.

Furthermore, the recess where the pharmaceutical delivery device is deposited may be on the medial, lateral, anterior, or posterior aspect of the polyethylene part. It may be created on a flat or round surface. It may be on either the topside or undersurface of the polyethylene part on a non weight-bearing surface. This is not an exhaustive list of possible locations for the recess. A person versed in the art can easily find a location which is not on this list but can accommodate the recess, which would not be on a weight-bearing surface of the polyethylene part, nor would it affect the mechanical properties or wear characteristics of the polyethylene part.

In one embodiment, multiple recesses and pharmaceutical delivery devices can be used and located in different surfaces of the polyethylene part. The number of recesses and devices and their locations are only limited to the desired pharmacological or physiological responses.

The recess can be in any shape. In one embodiment, the recess can be rectangular with grooves routed on the sidewalls to receive the ribs of a similarly rectangular pharmaceutical delivery device. In another embodiment, the rectangular pharmaceutical delivery device can be held in the rectangular recess by adhesive coated on the walls of the recess.

In yet another embodiment, the recess can be trapezoidal with or without grooves on the sidewalls. The pharmaceutical deliver device can be trapezoidal, whose top can be flush with the polyethylene part's surface or exposed to the joint space. The delivery device can also be triangular with the top exposed to the joint space and the bottom deposited in the trapezoidal recess.

In yet another embodiment, the recess can be cylindrical to accommodate a round rod shaped pharmaceutical delivery device.

It is appreciated that whatever shape of the recess and delivery device, a plurality of construction techniques, such as rib-groove, friction fit, adhesive, etc., can be used to hold the delivery device in the recess.

An exemplary recess may be 2-4 mm deep and the pharmaceutical delivery device may be flush with the side of the polyethylene part or extend out from the surface to the joint space. It is appreciated that how much exposed surface the pharmaceutical delivery device has with the joint space can be calculated and used as way to control the release rate of the pharmaceutical. A person versed in the art can create a recess larger than 4 mm in an area that does not affect the mechanical properties or wear characteristics of the part. This said area may include the top side of the polyethylene between the weight bearing surfaces of the femoral condyles, or the inner surfaces of the polyethylene parts where they are designed and made of 2 separate parts.

In one exemplary embodiment, the pharmaceutical delivery device may have a shape of a rod. Each recess can accommodate one rod. Multiple recesses, and rods, can be placed on the same surface or on different surfaces. The recesses and rods will not affect the mechanical properties or wear characteristics of the polyethylene part.

Each rod can contain the same or different pharmaceutical at same or different locations. The possible combinations of pharmaceutical rods are only limited by desired pharmacological and/or physiological responses.

It is appreciated that the pharmaceutical delivery device can be in a plurality of shapes to fit the shapes of the recesses described above.

The rod delivery device can be made of polymer that is mixed with a pharmaceutical heterogeneously or homogenously and introduced into the recess and held into place with a friction fit, adhesive, rib-groove or other construction techniques. In another embodiment, the rod can be made of silicon.

The pharmaceutical can be released through the end of the rod only, through the side of the rod which is exposed to joint fluid, or both.

If a retardant is used, it may encase the rod, or it may cover the end of the rod on one or both sides. The retardant coverage and/or location can be calculated as to control the release rate of the pharmaceutical for desired pharmacological and/or physiological responses.

DETAIL DESCRIPTION OF THE DRAWINGS

FIG. 1 is an illustrative overview of a total knee replacement system, including the femoral component 100, the polyethylene insert 101, and the tibial component 102. The proposed site 103 for the pharmaceutical delivery system is located at the polyethylene insert 101.

Figure 2:
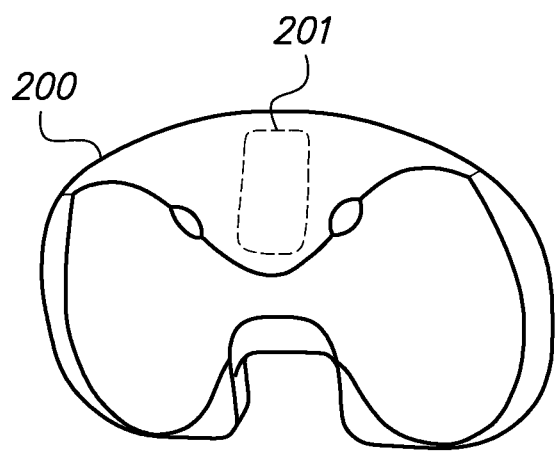
FIG. 2 is an illustration of a top view of a cruciate-retaining tibial liner of a knee replacement part with targeted area of pharmaceutical delivery device.

FIG. 2 illustrates a top view of a cruciate-retaining tibial liner 200, in which the proposed site 201 of pharmaceutical delivery system is located. The cruciate-retaining tibial liner 200 described herein is the same component as that found in the FIG. 1 described above.

Figure 3:
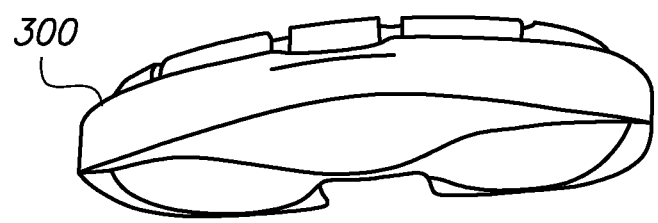
FIG. 3 is an illustration of a front view of a cruciate-retaining tibial liner of a knee replacement part with targeted area of pharmaceutical delivery device.

FIG. 3 illustrates a front view of a cruciate-retaining tibial liner 300, the same component as described in FIG. 2 and found as part of the total knee replacement system described in FIG. 1.

Figure 4:
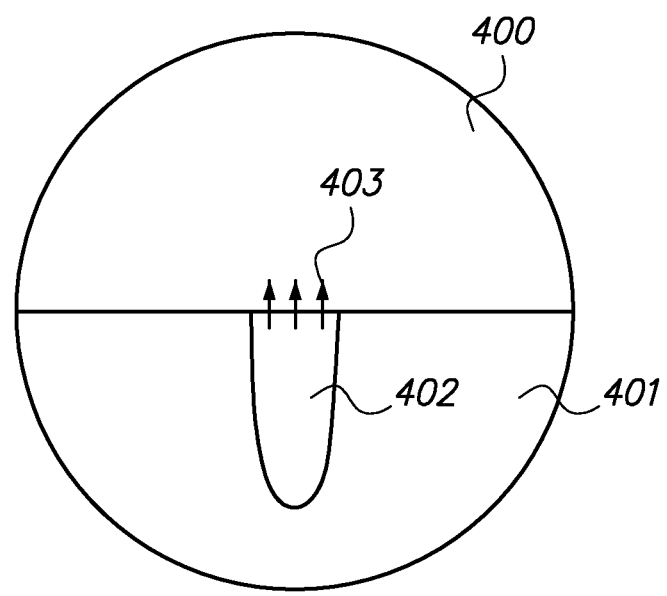
FIG. 4 is a close up diagram representation of the pharmaceutical delivery system functioning within a joint replacement part.

FIG. 4 is a close up diagram representation of the pharmaceutical delivery device 402 functioning within joint replacement parts, wherein the pharmaceutical delivery system 402 resides in a space inside the polyethylene liner 401. Because the pharmaceutical delivery device allows for the diffusion of pharmaceutical agents from areas of high concentration to areas of low concentration, the pharmaceutical drugs will diffuse out 403 from the pharmaceutical delivery device 402 which has a high concentration towards the effective joint space 400 which a low pharmaceutical concentration.

Figure 5:
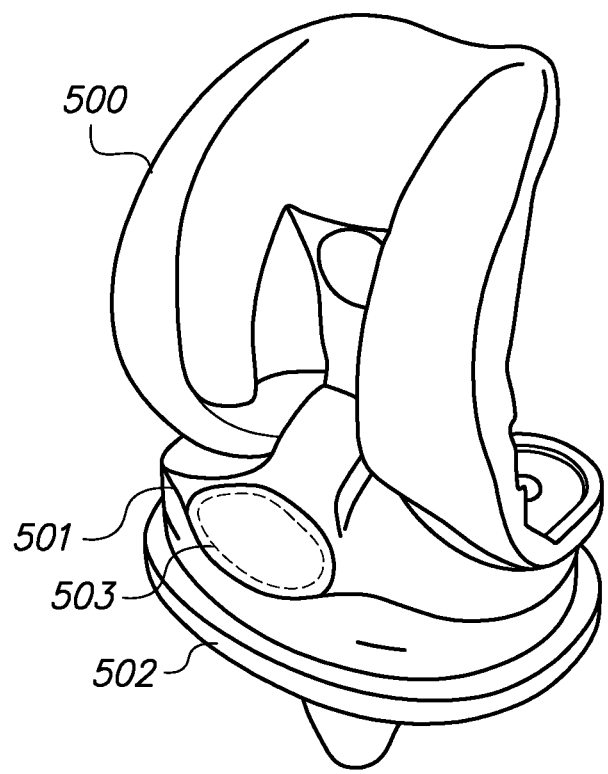
FIG. 5 is an illustration of a front view of a posterior-stabilized tibial liner in vivo of total knee replacement with targeted area of pharmaceutical delivery device.

FIG. 5 illustrates a front view of a posterior-stabilized tibial liner in vivo, wherein there is a femoral component 500, a posterior stabilized tibial insert 501, and a tibial component 502. The proposed site 503 of the pharmaceutical delivery system is located at a space within the posterior stabilized tibial insert 501.

Figure 6:
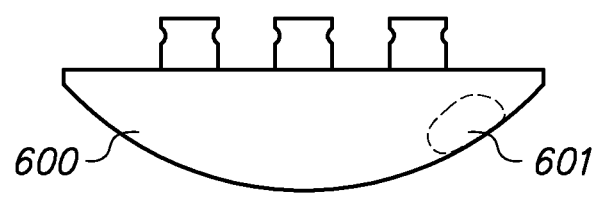
FIG. 6 is an illustration of a side view of a Patellar button of a knee replacement with targeted area of pharmaceutical delivery device.

FIG. 6 illustrates a side view of a Patellar button 600, wherein the targeted area 601 of the pharmaceutical delivery system is located.

Figure 7:
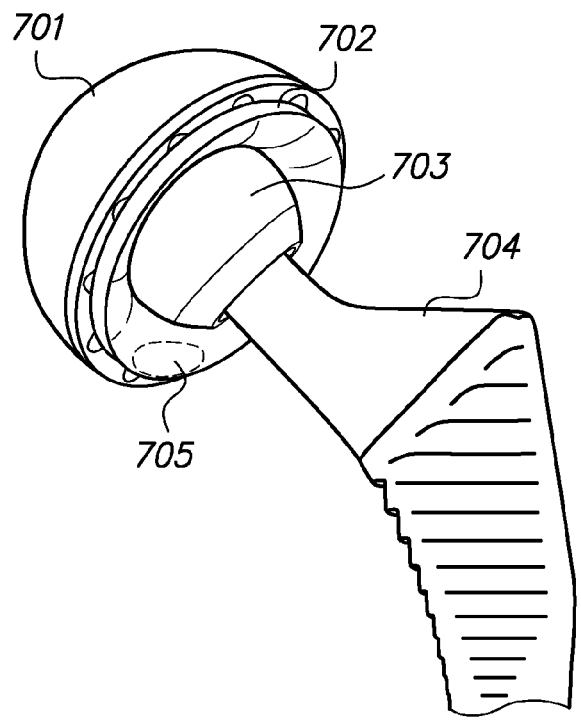
FIG. 7 is an illustration of a hip replacement part in vivo with targeted area of pharmaceutical delivery device.

FIG. 7 illustrates a front view of a hip replacement part 700 in vivo, including the Acetabular cup 701, the Acetabular liner 702, the prosthetic head 703, and the femoral stem 704, wherein the targeted area 705 of the pharmaceutical delivery system is located.

Figure 8:
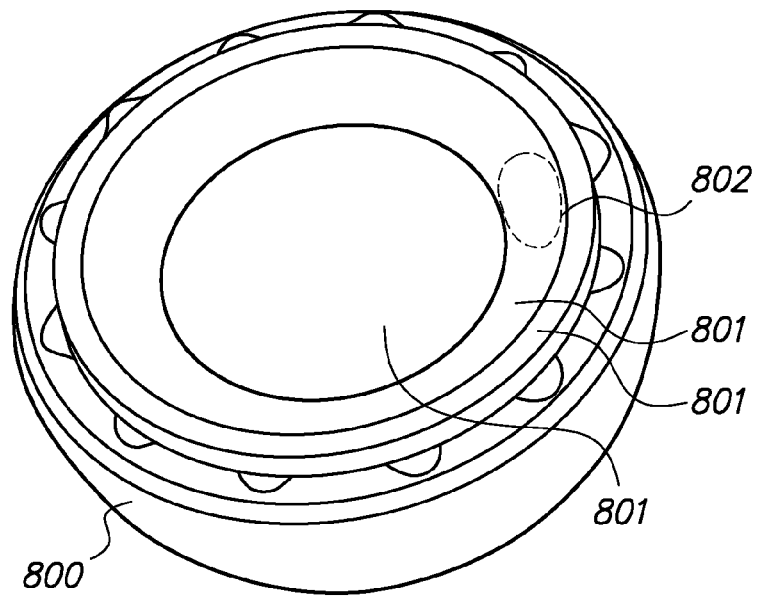
FIG. 8 is an illustration of a front view of an Acetabular liner of a hip replacement with targeted area of pharmaceutical delivery device.

FIG. 8 illustrative of a front view of an Acetabular liner 800 of a hip replacement, wherein there is an Acetabular insert 801 and a targeted site 802 of the pharmaceutical delivery system.

Figure 9:
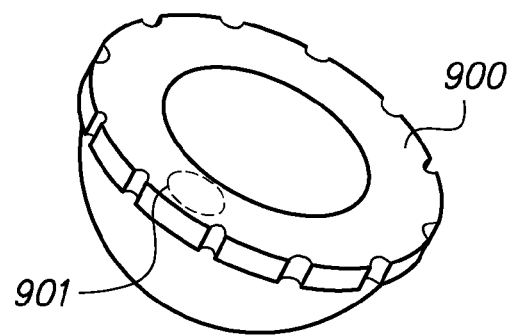
FIG. 9 is an illustration of a side view of an Acetabular lipped-liner of a hip replacement with targeted area of pharmaceutical delivery device.

FIG. 9 illustrates a side view of an Acetabular lipped-liner 900 of a hip replacement, wherein a targeted site 901 of the pharmaceutical delivery system is located.

Figure 10:
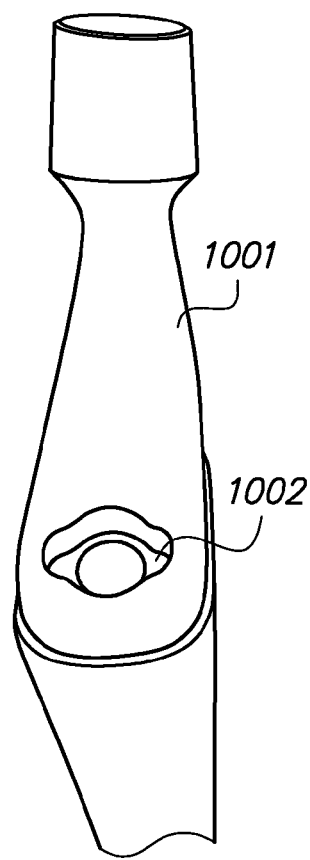
FIG. 10 is an illustration of a top view of a naturally occurring space in a hip stem of a hip replacement with targeted area of pharmaceutical delivery device.

FIG. 10 illustrates a top view of a naturally occurring space of a hip stem in a hip replacement system 1000, wherein there is a hip femoral stem 1001 and a targeted area 1002 of pharmaceutical delivery system.

Figure 11:
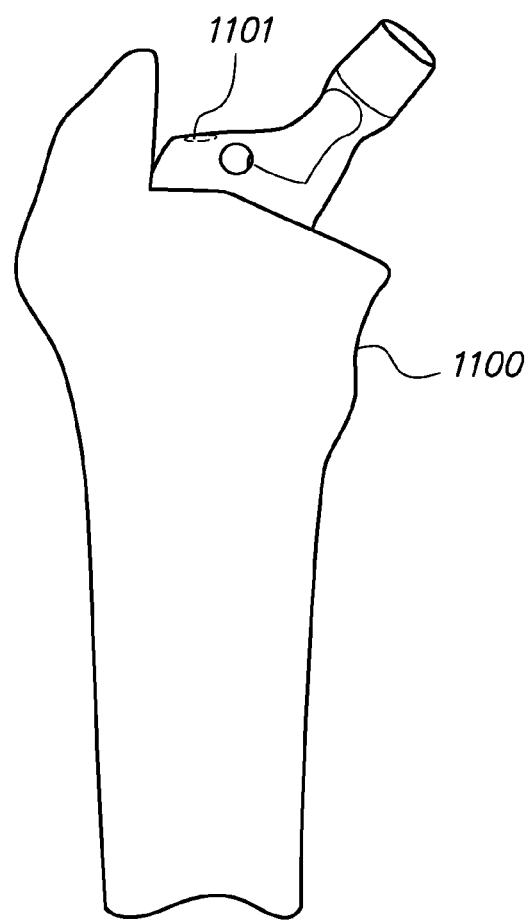
FIG. 11 is an illustration of a top view of a naturally occurring space in a tibial component in a hip replacement with targeted area of pharmaceutical delivery device.

FIG. 11 illustrates the top view of a naturally occurring space in a tibial component, wherein the site 1101 of pharmaceutical delivery system is located in a naturally occurring space within the hip femoral stem 1100.

Figure 12:
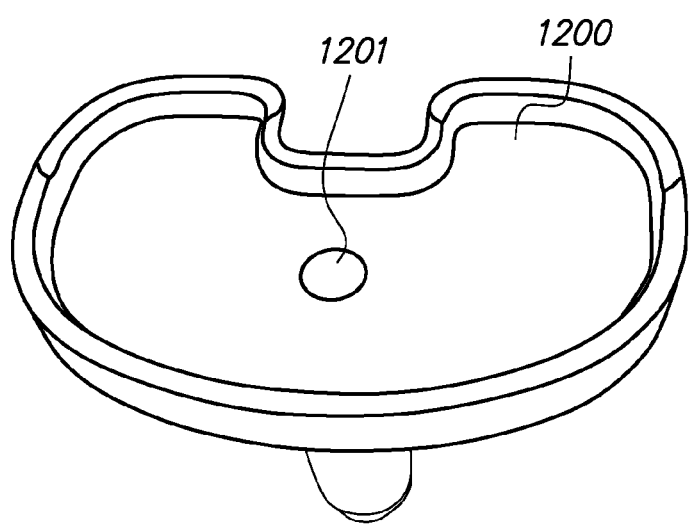
FIG. 12 is an illustrative view of the tibial tray with targeted area of the pharmaceutical delivery device.

FIG. 12 illustrates a perspective view of the tibial tray 1200, wherein the site 1201 of the pharmaceutical delivery system is located in a naturally occurring space in the tibial tray 1200.

Figure 13:
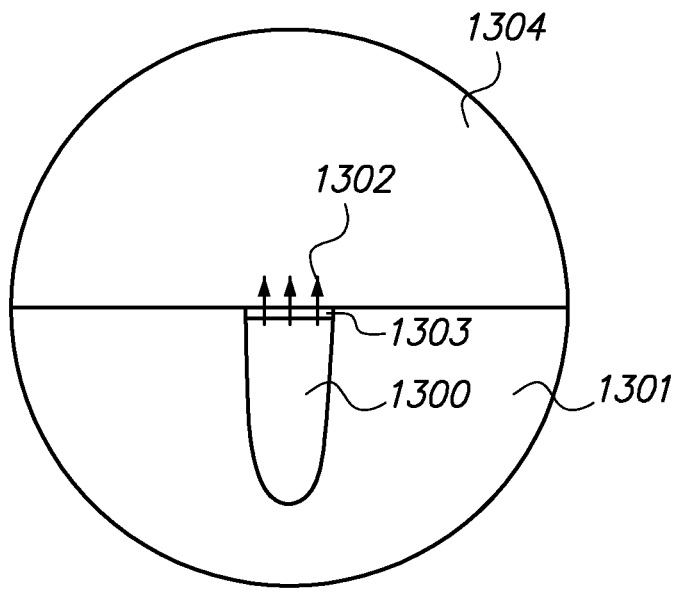
FIG. 13 is a close up diagram representation of the pharmaceutical delivery device using a layer of retardant.

FIG. 13 is a diagram representation of the pharmaceutical delivery system 1300 located within a space in the polyethylene 1301, wherein the pharmaceutical drug diffuses 1302 from area of high concentration inside the pharmaceutical delivery system 1300 through a retardant 1303 to an area of low concentration in the effective joint space 1304.

Figure 14:
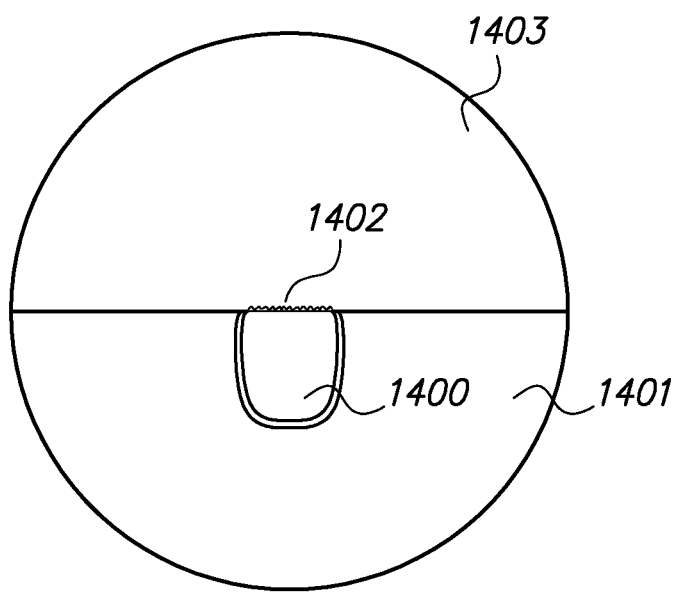
FIG. 14 is an illustration of the pharmaceutical delivery system using polyethylene that has been previously treated with a pharmaceutical.

FIG. 14 is a diagram representation of the pharmaceutical delivery system 1400 located within a space in the polyethylene 1401, wherein the pharmaceutical delivery system is previously treated with a pharmaceutical. Furthermore, the site of diffusion for the pharmaceutical drug is coated with antibiotic 1402 and the pharmaceutical drug diffuses from an area of low concentration to an area of high concentration into the effective joint space 1403.

Figure 15:
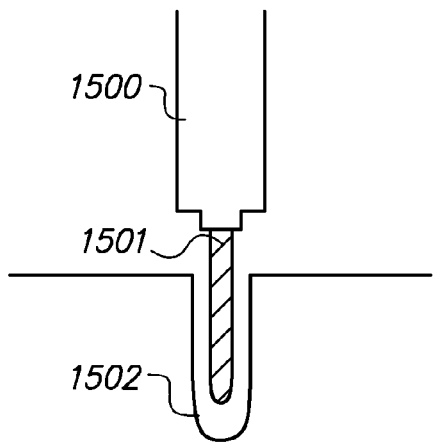
FIG. 15 is an illustration of a drill forming the recesses in replacement parts of a joint replacement system wherein the pharmaceutical delivery system may be inserted

FIG. 15 illustrates the use of a drill mechanism 1500 making an artificial space 1502 in a joint replacement part, wherein the drill 1501 is used to create the appropriate space for insertion of the pharmaceutical delivery device.

Figure 16:
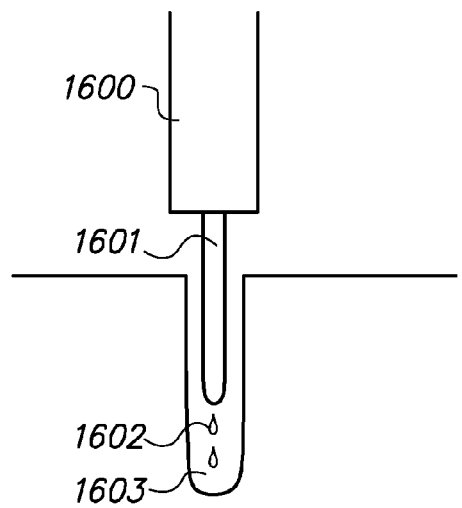
FIG. 16 is an illustration of the addition of adhesive into the recesses form in the replacement parts of a joint replacement system

FIG. 16 illustrates the addition of adhesives 1602 into the artificially created space 1603, wherein the adhesive is administered by an adhesive needle or device 1600 with a guiding release mechanism 1601 for accuracy and ease of use.

Figure 17:
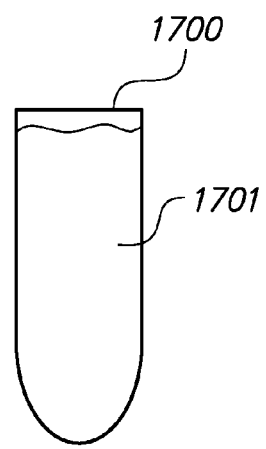
FIG. 17 is an illustration of an encapsulated pharmaceutical.

FIG. 17 illustrates the encapsulated pharmaceutical wherein the pharmaceutical 1701 is encapsulated by retardants 1700 to form the desired shape.

Figure 18:
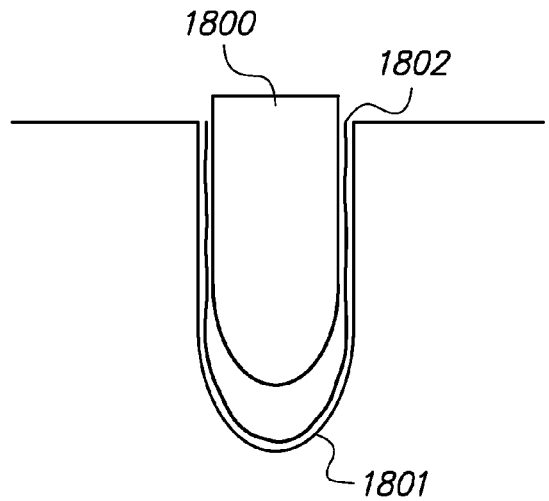
FIG. 18 is an illustration of the introduction, via the adhesive method, of an encapsulated pharmaceutical into the recesses of the replacement part of a joint replacement system.

FIG. 18 illustrates the insertion of the encapsulated pharmaceutical delivery device 1800 into the artificially created space 1801, wherein the encapsulated pharmaceutical device 1800 is held in place with the use of adhesives 1802.

Figure 19:
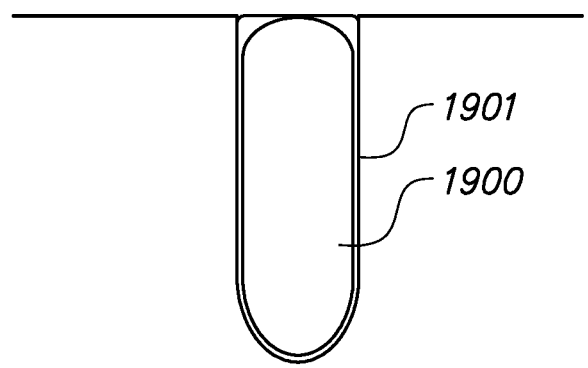
FIG. 19 is an illustration of the introduction, via the press fit method, of an encapsulated pharmaceutical into the recesses of the replacement part of a joint replacement system.

FIG. 19 illustrates the insertion of the encapsulated pharmaceutical delivery device 1900 into the artificially created space 1901 through the press fit method, wherein the fit of the encapsulated pharmaceutical device 1900 and the artificially created space 1901 is perfectly matched such that the friction between them keeps each other in place.

Figure 20:
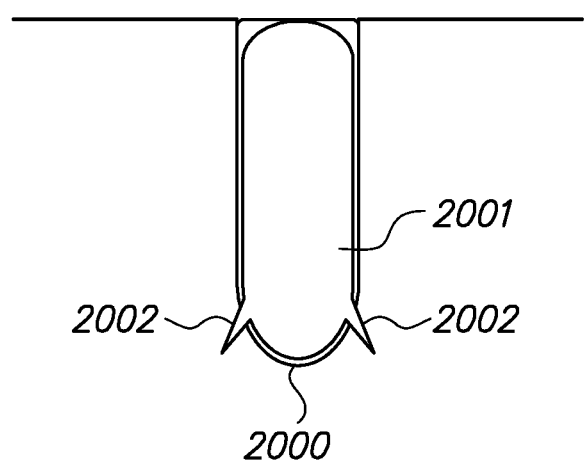
FIG. 20 is an illustration of the introduction of an encapsulated pharmaceutical into the recesses of the replacement part of a joint replacement system and secured by the retardant.

FIG. 20 illustrates the insertion of the encapsulated pharmaceutical delivery device 2001 into the artificially created space 2000 through the use of anchors 2002, wherein the anchors 2002 are part of the retardant used to encapsulate and create the pharmaceutical delivery device.

Figure 21:
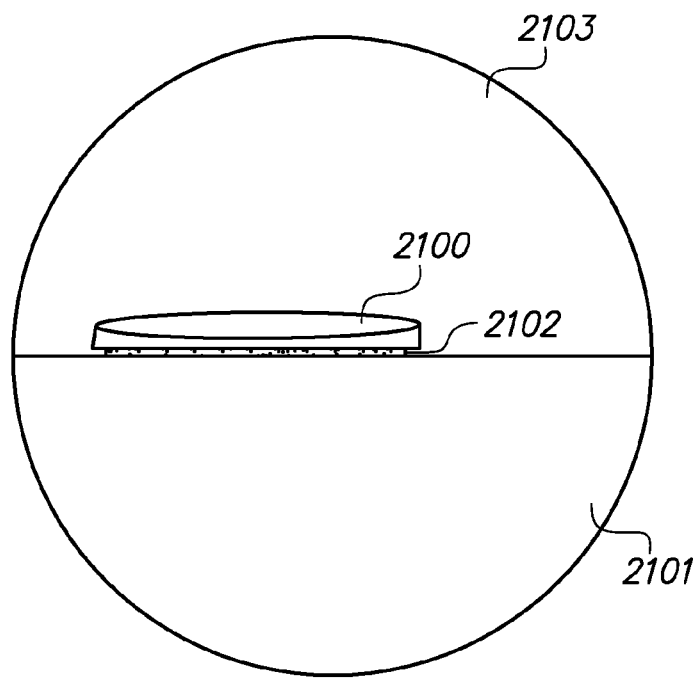
FIG. 21 is an illustration of a mound shaped pharmaceutical delivery system attached via an adhesive onto a joint replacement part.

FIG. 21 illustrates the attachment of the pharmaceutical delivery device 2100 onto the joint replacement part 2101 via the use of adhesives 2102, wherein the pharmaceutical delivery device 2100 can be any shape, such as mound shaped. The pharmaceutical delivery device 2100 attaches to a non-weight bearing area of the joint replacement part 2101 and the pharmaceutical will diffuse through the retardant into the effective joint space 2103.

Figure 22:
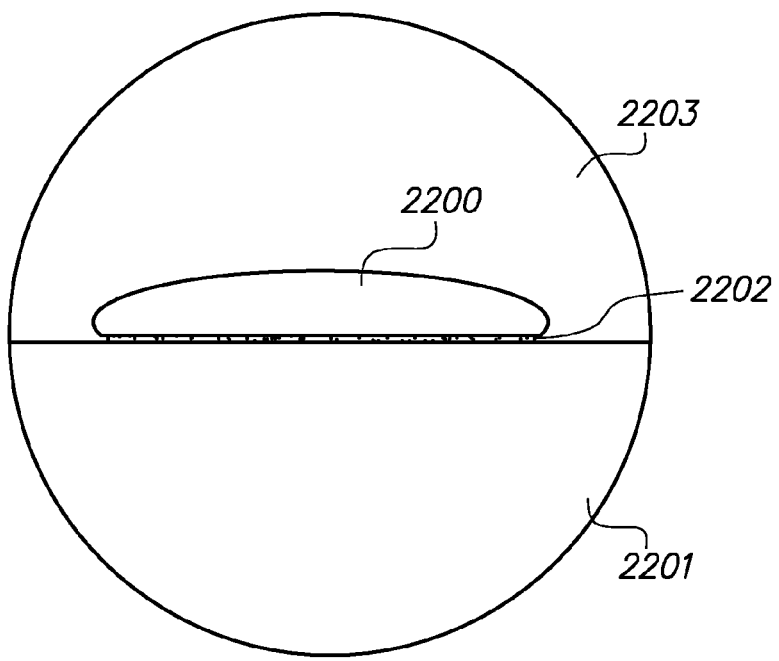
FIG. 22 is an illustration of a rectangular shaped pharmaceutical delivery system attached via an adhesive onto a joint replacement part.

FIG. 22 illustrates a box shaped pharmaceutical delivery system 2200 using the same methodology as described for FIG. 21, wherein the pharmaceutical delivery system 2200 is attached onto the joint replacement part 2201 via the use of adhesives 2202. The pharmaceutical delivery device 2200 also attached to a non-weight bearing area of the joint replacement part 2201 and the pharmaceutical inside the pharmaceutical delivery device 2200 will diffuse through the retardant and into the effective joint space 2203.

Figure 23:
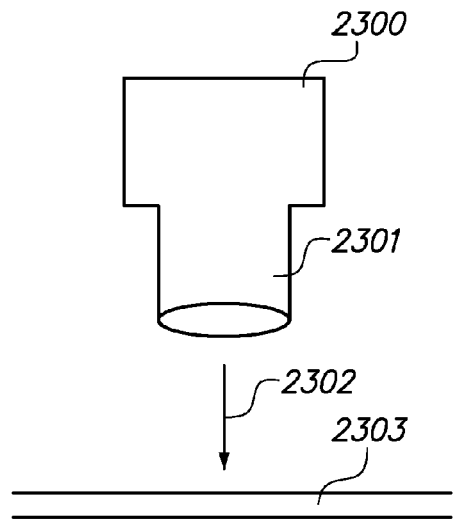
FIG. 23 is an illustration of the use of a cylindrical machining device against a polyethylene layer of a joint replacement part.

FIG. 23 illustrates a machining device 2300 with a cylindrical shape 2301 to be used 2302 against the polyethylene area 2303 of a joint replacement part.

Figure 24:
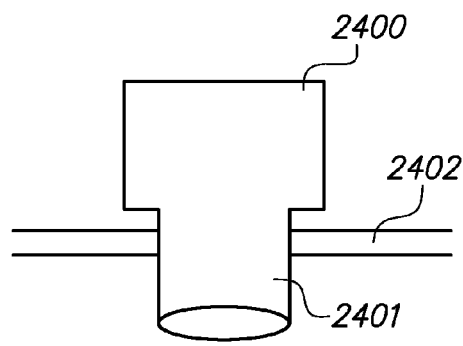
FIG. 24 is an illustration of the use of a cylindrical machining device to core out a cylindrical artificial recess against the polyethylene in a joint replacement part.

FIG. 24 illustrates the use of a machining device 2400 with a cylindrical shape 2401 against the polyethylene area 2402 of a joint replacement part.

Figure 25:
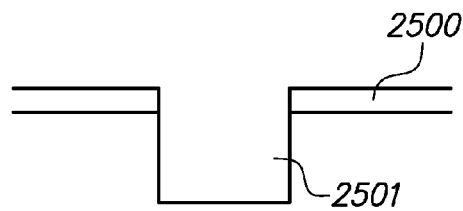
FIG. 25 is an illustration of the cylindrical artificial recess in the joint replacement part created by the cylindrical machining device.

FIG. 25 illustrates the cylindrical artificial recess formed 2501 on the polyethylene area 2500 of a joint replacement part.

Figure 26:
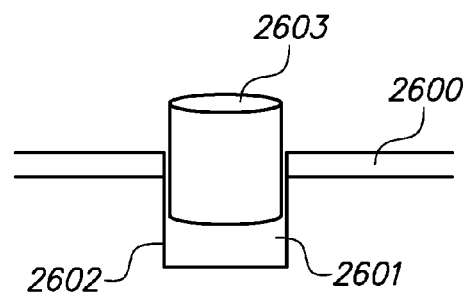
FIG. 26 is an illustration of a cylindrical pharmaceutical delivery system being attached to the cylindrical recess in the joint replacement part.

FIG. 26 illustrates the attachment of the cylindrical pharmaceutical delivery device 2603 into the cylindrical artificial recess 2601 of the joint replacement part 2600 via press fit or adhesive 2602.

Figure 27:
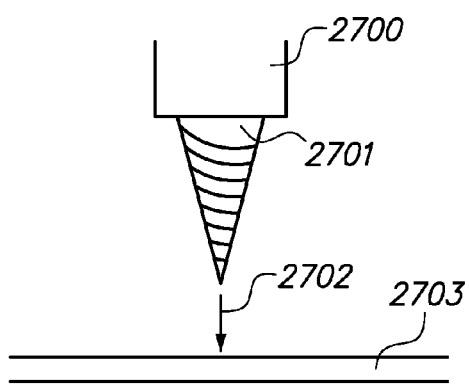
FIG. 27 is an illustration of the use of a conical machining device against a polyethylene layer of a joint replacement part.

FIG. 27 illustrates a machining device 2700 with a conical shape 2701 to be used 2702 against the polyethylene area 2703 of a joint replacement part.

Figure 28:
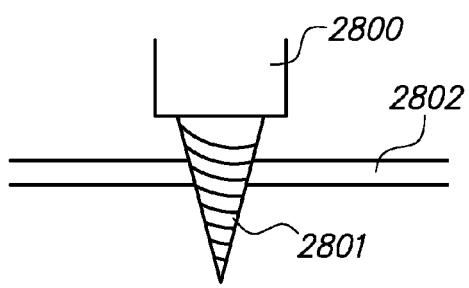
FIG. 28 is an illustration of the use of a conical machining device to core out a conical artificial recess against the polyethylene in a joint replacement part.

FIG. 28 illustrates the use of a machining device 2800 with a conical shape 2801 against the polyethylene area 2802 of a joint replacement part.

Figure 29:
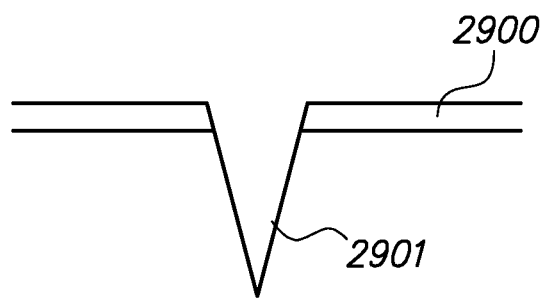
FIG. 29 is an illustration of the conical artificial recess in the joint replacement part created by the conical machining device.

FIG. 29 illustrates the conical artificial recess formed 2901 on the polyethylene area 2900 of a joint replacement part.

Figure 30:
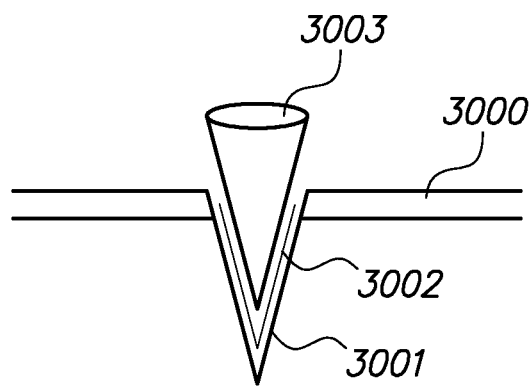
FIG. 30 is an illustration of a conical pharmaceutical delivery system being attached to the conical recess in the joint replacement part.

FIG. 30 illustrates the attachment of the conical pharmaceutical delivery device 3003 into the conical artificial recess 3001 of the joint replacement part 3000 via press fit or adhesive 3002.

FIG. 31 illustrates the top view of an exemplary polyethylene insert 103, comprising posterior part 3101, anterior part 3102, medial part 3103, lateral part 3104, the weight bearing surface 3105, the non weight bearing surfaces 3106 and 3107. These are the exemplary locations where a recess or recesses can be created. This list is not exhaustive.

FIG. 32 illustrates the front view of the polyethylene part 103 wherein the top surface 3201 and undersurface 3202 are other exemplary locations where a recess or recesses can be created.

FIG. 33 illustrates the close-up of a usable surface of the polyethylene part 103 wherein a recess 3301 is created.

FIG. 34 illustrates an exemplary polymer rod 3400 carrying pharmaceutical as an exemplary pharmaceutical delivery device. It is appreciated that a rod does not have to be polymer or round as in this embodiment. The rod has a side surface 3401, one end 3402, and other end 3403. The pharmaceutical can be released from one, two, or all parts of the rod. In this embodiment, the pharmaceutical is being released through end 3403 of the rod.

FIG. 35 illustrates the cross section of the rod 3400, wherein the pharmaceutical can be released through the body of the rod in this embodiment.

FIG. 36 illustrates the cross section of the rod 3400 with retardant layer 3601 encasing the rod in this embodiment. The retardant layer 3601 controls the release rate of the pharmaceutical from the rod.

FIG. 37 illustrates the side view of the rod 3400, which in this embodiment has a retardant cap 3701 on one end of the rod, which controls the release rate of the pharmaceutical.

FIG. 38 illustrates a rod 3400 within the groove. The rod in this embodiment is held in the groove with friction fit 3801. The arrows depict the expected directions of pharmaceutical releases. The surface of rod exposed can be calculated to control the release rate of the pharmaceutical.

FIG. 39 illustrates the rod 3400 that in this embodiment is glued to the recess by an adhesive 3901.

FIG. 40 illustrates the front view of a polyethylene part 103, and, in this embodiment, the appearance of a rod 3400 in the front surface.

FIG. 41 illustrates the side view of a polyethylene part 103 with, in this embodiment, a rod 3400 in the side surface.

FIG. 42 illustrates, in this embodiment, multiple rods 3400 within a polyethylene part 103.

FIG. 43 illustrates the top surface of a polyethylene part 103 with, in this embodiment, a single rod 3400 in between the weight bearing surfaces.

Figure 44:
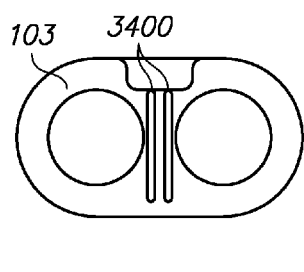
FIG. 44 illustrates the top surface of a polyethylene part with two rods in place.

FIG. 44 illustrates the top surface of a polyethylene part 103 with, in this embodiment, two rods 3400 in between the weight bearing surfaces.

Figure 45:
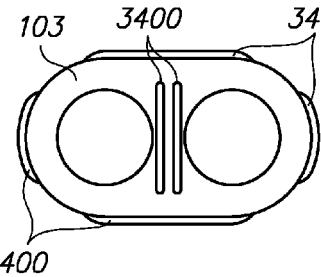
FIG. 45 illustrates the top view of a polyethylene part with top surface rods, and medial, lateral, anterior and posterior rods.

FIG. 45 illustrates the top surface of a polyethylene part 103 with, in this embodiment, rods 3400 in the top, posterior 3101, anterior 3102, medial 3103, and lateral 3104 surfaces. It is appreciated that all rods or any combination of them can be used to achieve pharmacological and physiological responses.

Figure 46:
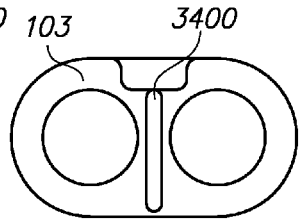
FIG. 46 illustrates the top view of a polyethylene part with a larger rod placed in the non weight bearing top surface.

FIG. 46 illustrates the top surface of a polyethylene part 103 with, in this embodiment, a larger rod 3400 in between the weight bearing surfaces.

Figure 47:
FIG. 47 illustrates the coronal cross section of a polyethylene part and rod in the non weight bearing top surface.

FIG. 47 illustrates the coronal cross section of a polyethylene part 103 and a rod 3400 in the top surface of the polyethylene part.

Figure 48:
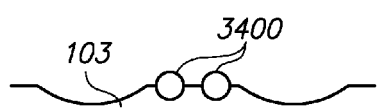
FIG. 48 illustrates the coronal cross section of a polyethylene part and multiple rods in the non weight bearing top surface.

FIG. 48 illustrates the coronal cross section of a polyethylene part 103 and multiple rods 3400.

Figure 49:
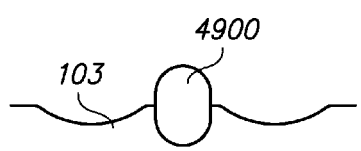
FIG. 49 illustrates the coronal cross section of a polyethylene part and an oblong shaped rod.

FIG. 49 is the coronal cross section of a polyethylene part 103 and an oblong-shaped rod 4900.

Figure 50:
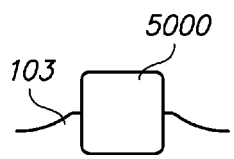
FIG. 50 illustrates the coronal cross section of a polyethylene part and a 4-sided polymer rod.

FIG. 50 is the coronal cross section of a polyethylene part 103 and a 4-sided polymer rod 5000.

Figure 51:
FIG. 51 illustrates the coronal cross section of a polyethylene part and a 3-sided polymer rod.

FIG. 51 is the coronal cross section of a polyethylene part 103 and a 3 sided polymer rod 5100.

Figure 52:
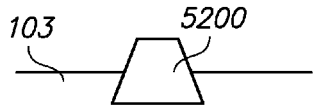
FIG. 52 illustrates the coronal cross section of a polyethylene part and a trapezoidal 4-sided polymer rod.

FIG. 52 is the coronal cross section of a polyethylene part 103 and a trapezoidal 4 sided polymer part 5200.

Figure 53:
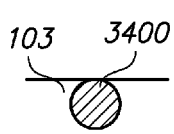
FIG. 53 illustrates the coronal cross section of a polyethylene part and a rod flush with the polyethylene part.

FIG. 53 is the coronal cross section of a polyethylene part 103 and a rod 3400 flush with the polyethylene.

Figure 54:
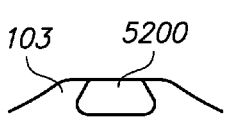
FIG. 54 illustrates the coronal cross section of a polyethylene part and a trapezoidal polymer rod flush with the polyethylene part.

FIG. 54 is the coronal cross section of a polyethylene part 103 and a trapezoidal polymer rod 5200 flush with the polyethylene.

Figure 55:
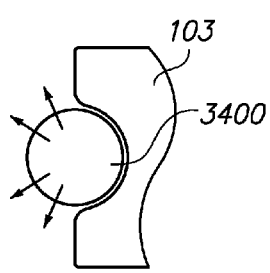
FIG. 55 illustrates the cross section of a polyethylene part and a rod with pharmaceutical being diffused from the side of the rod into the joint space.

FIG. 55 is the cross section of a polyethylene part 103 and a rod 3400 with pharmaceutical being diffused from the side of the rod into the joint space. The exposed surface of the rod can control the release rate of the pharmaceutical. The arrows represent the direction of the diffusion of the pharmaceutical.

Figure 56:
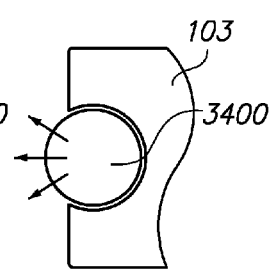
FIG. 56 illustrates the cross section of a polyethylene part and a rod with pharmaceutical being diffused from a smaller surface area of the rod.

FIG. 56 is the cross section of a polyethylene part 103 and a rod 3400 with drug being diffused from a smaller surface of the rod. It is appreciated that the rod's surface exposed to joint fluid can be intentionally adjusted to control the release rate of the pharmaceutical.

Figure 57:
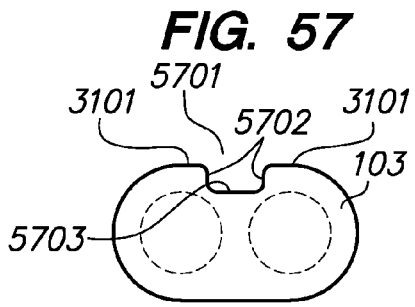
FIG. 57 illustrates the top view of a polyethylene part with a recess on the posterior surface of the polyethylene part.

FIG. 57 illustrates the top view of a polyethylene part 103, and a posterior recess 5701 in the posterior surface 3101 and the recess's side walls' 5702 and back wall's 5703 surfaces available for use.

Figure 58:
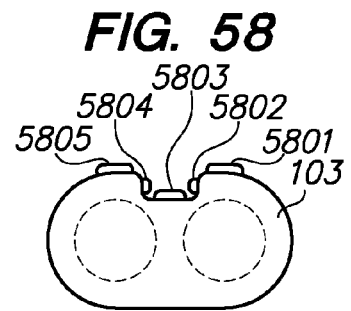
FIG. 58 illustrates the top view of a polyethylene part with a plurality of pharmaceutical delivery devices deposited on a plurality of surfaces of the polyethylene part.

FIG. 58 illustrates the top view of a polyethylene part 103 with a posterior recess 5701 created, and a plurality of pharmaceutical delivery devices present on several surfaces of the polyethylene part and the recess. Delivery devices 5801 and 5805 are posteriorly mounted. Delivery devices 5802 and 5804 are posterior recess's sidewall mounted. Deliver device 5803 is posterior recess's back-wall mounted, in the deepest place of the posterior recess.

Figure 59:
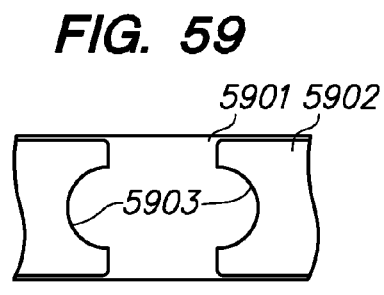
FIG. 59 illustrates the blowup of a posterior recess with grooves on the side walls thereof.

FIG. 59 illustrates the close up of a posterior recess with grooves on the side walls, and the deepest surface of the posterior recess 5901, the posterior surface of the polyethylene part 103 5902, and the grooves in the sidewalls of the posterior recess 5903.

Figure 60:
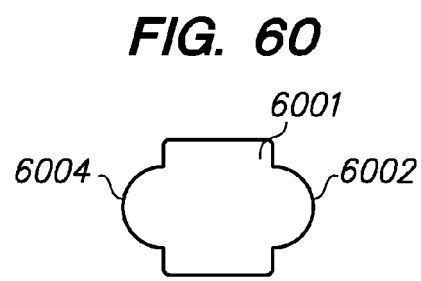
FIG. 60 illustrates a rectangular-shaped pharmaceutical delivery device with ribs that mate with the grooves in the posterior recess of a polyethylene part.

FIG. 60 illustrates a rectangularly shaped pharmaceutical delivery device 6001 with ribs 6002 and 6004 that mate with the grooves in the posterior recess of the polyethylene.

Figure 61:
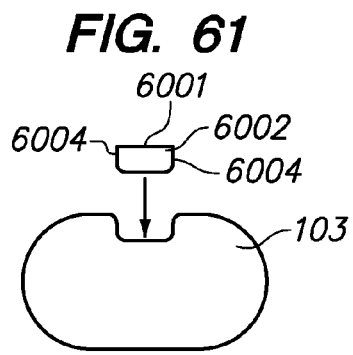
FIG. 61 illustrates the top view of a polyethylene part with a rectangular-shaped pharmaceutical delivery device being inserted into the posterior recess and its ribs mating with the grooves on the walls of the posterior recess.

FIG. 61 illustrates the top view of a polyethylene part 103 with the rectangularly shaped pharmaceutical delivery device 6001 being inserted into a posterior recess mating the grooves in the sidewalls of the posterior recess with the ribs 6002, 6004 of the pharmaceutical delivery device.

Figure 62:
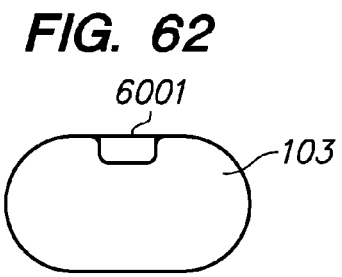
FIG. 62 illustrates the top view of a polyethylene part with a rectangular-shaped pharmaceutical delivery device mated with it.

FIG. 62 illustrates the top view of a polyethylene part 103 with the rectangularly shaped pharmaceutical delivery device 6001 mated with it.

Figure 63:
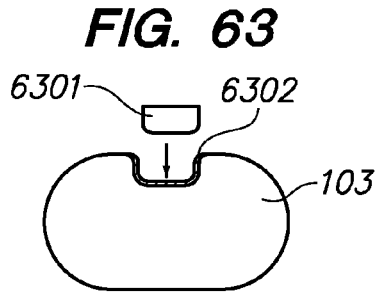
FIG. 63 illustrates the top view of a polyethylene part with a rectangular shaped pharmaceutical delivery device being inserted in a posterior recess of the polyethylene part coated with adhesive.

FIG. 63 illustrates the top view of a polyethylene part 103 with the rectangularly shaped pharmaceutical delivery device 6001 being inserted into a posterior recess coated with adhesive 6302.

Figure 64:
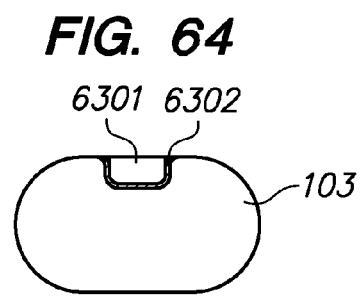
FIG. 64 illustrates the top view of a polyethylene part with a rectangular shaped pharmaceutical delivery device being held in a posterior recess of the polyethylene part with an adhesive.

FIG. 64 illustrates the top view of a polyethylene part 103 with the rectangularly shaped pharmaceutical delivery device 6001 held in a posterior recess with adhesive 6302.

Figure 65:
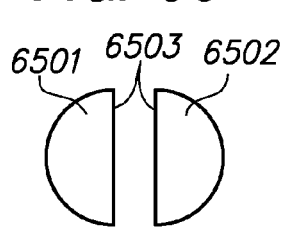
FIG. 65 illustrates the top view of medial and lateral polyethylene parts.

FIG. 65 illustrates the top view of lateral and medial polyethylene parts 6501 and 6502, respectively. The inner surfaces 6503 of said parts facing each other.

Figure 66:
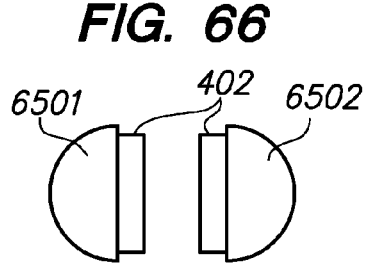
FIG. 66 illustrates the top view of medial and lateral polyethylene parts with a pharmaceutical delivery device mounted on the inner surfaces of both parts.

FIG. 66 illustrates the top view of medial and lateral polyethylene parts 6501 and 6502 with pharmaceutical delivery devices 402 mounted on the inner surfaces 6503 of said parts.

FIG. 67 illustrates an angular view of the face of a polyethylene hip replacement part 6701 with pharmaceutical delivery devices 402 affixed to said part's lip 6702.

FIG. 68 illustrates an angular view of the face of a polyethylene hip replacement part 6701 with multiple shorter delivery devices 402 affixed to said part on its lip 6702.

The invention claimed is:

1. A drug delivery system for the sustained administration of a pharmaceutical into a joint replacement at a controlled rate to produce a beneficial response, said device comprising:
   a. a plurality of bodies comprising at least one portion of pharmaceutical composition mixed with at least one portion of polymer composition;
   b. a joint replacement having multiple inserts wherein said inserts are drilled to cause a plurality of openings to accommodate said plurality of bodies;
   c. wherein said plurality of bodies are placed inside said plurality of openings without interfering with said joint replacement's normal operation;
   d. a plurality of membranes sealing said plurality of bodies within said plurality of openings;
   e. wherein said plurality of membranes are comprised of a material which allows for said pharmaceutical to diffuse across said plurality of membranes;
   f. wherein said material further determines the diffusion rate of said pharmaceutical crossing said plurality of membranes.

2. The drug delivery system of claim 1 wherein said plurality of bodies are in the shape of cylinders.

3. The drug delivery system of claim 2 wherein said material encases said plurality of bodies.

4. The drug delivery system of claim 2 wherein said material is located at the opposite ends of said cylinders.

5. The drug delivery system of claim 1 wherein said plurality of bodies are held inside said plurality of openings base on the friction created as a result of a tight fit between said plurality of bodies and said plurality of openings.

* * * * *